(12) United States Patent
Roeder et al.

(10) Patent No.: US 10,478,591 B2
(45) Date of Patent: Nov. 19, 2019

(54) STENT GRAFT DELIVERY DEVICE PRE-LOADED WITH A SINGLE WIRE FOR DEVICE TRACKING AND CANNULATION

(71) Applicant: COOK MEDICAL TECHNOLOGIES LLC, Bloomington, IN (US)

(72) Inventors: Blayne A. Roeder, Bloomington, IN (US); Jarin Kratzberg, Lafayette, IN (US); Erik E. Rasmussen, Slagelse (DK); Derek R. Eller, Bloomington, IN (US); Saylan Lukas, Cincinnati, OH (US)

(73) Assignee: Cook Medical Technologies LLC, Bloomington, IN (US)

( * ) Notice: Subject to any disclaimer, the term of this patent is extended or adjusted under 35 U.S.C. 154(b) by 445 days.

(21) Appl. No.: 15/010,613

(22) Filed: Jan. 29, 2016

(65) Prior Publication Data
US 2016/0256304 A1 Sep. 8, 2016

Related U.S. Application Data

(60) Provisional application No. 62/128,705, filed on Mar. 5, 2015.

(51) Int. Cl.
*A61M 25/00* (2006.01)
*A61F 2/07* (2013.01)
(Continued)

(52) U.S. Cl.
CPC .......... *A61M 25/0068* (2013.01); *A61F 2/07* (2013.01); *A61F 2/966* (2013.01); *A61F 2/89* (2013.01);
(Continued)

(58) Field of Classification Search
CPC .. A61F 2/954; A61F 2/95; A61F 2/957; A61F 2/962; A61F 2/966; A61F 2/97;
(Continued)

(56) References Cited

U.S. PATENT DOCUMENTS 6,013,019 A * 1/2000 Fischell .................... A61F 2/95
600/1
7,435,253 B1 * 10/2008 Hartley .................... A61F 2/07
623/1.11
(Continued)

FOREIGN PATENT DOCUMENTS

| EP | 2471498 A1 | 7/2012 |
|----|------------|--------|
| EP | 2574306 A1 | 4/2013 |

(Continued)

OTHER PUBLICATIONS

European Search Report for Application No. EP 16275022, dated May 31, 2016, 8 pages.
European Search Report for Application No. EP 16158789, dated Jul. 13, 2016, 8 pages.

*Primary Examiner* — Diane D Yabut
*Assistant Examiner* — Lindsey Bachman
(74) *Attorney, Agent, or Firm* — Brinks Gilson & Lione (57) ABSTRACT

A stent graft delivery device that is pre-loaded with a single guide wire for both tracking the device within a main vessel as well as for cannulating one or more branch vessels is described. The delivery device comprises a delivery catheter having a prosthesis releasably secured thereto and a nose cone extending from the proximal end of the catheter. In a delivery configuration, a secondary catheter is coaxial with the guide wire and extends through at least a portion of the prosthesis lumen and is held within a channel formed in the nose cone. In a released configuration, secondary catheter and guide wire are retracted distally out of the channel (Continued)

formed in the sidewall of the nose cone dilator and can be manipulated for cannulating a branch vessel.

13 Claims, 8 Drawing Sheets

(51) Int. Cl.
    *A61F 2/966*     (2013.01)
    *A61F 2/06*     (2013.01)
    *A61F 2/89*     (2013.01)
    *A61F 2/97*     (2013.01)
    *A61M 29/00*     (2006.01)

(52) U.S. Cl.
    CPC ........... *A61F 2/97* (2013.01); *A61F 2002/061* (2013.01); *A61M 29/00* (2013.01)

(58) Field of Classification Search
    CPC .. A61M 2025/0169; A61M 2025/0172; A61M 2025/0183; A61M 25/007; A61M 25/0068
    See application file for complete search history.

(56) References Cited

U.S. PATENT DOCUMENTS

| | | |
|---|---|---|
| 7,611,529 B2 | 11/2009 | Greenberg et al. |
| 8,394,135 B2 | 3/2013 | Jensen et al. |
| 2005/0154440 A1* | 7/2005 | Limon .................. A61F 2/958 623/1.11 |
| 2007/0123910 A1* | 5/2007 | Hartley .................. A61F 2/954 606/108 |
| 2011/0125244 A1 | 5/2011 | Roeder et al. |
| 2012/0109056 A1 | 5/2012 | Rasmussen |
| 2012/0277848 A1 | 11/2012 | Roeder et al. |
| 2013/0123907 A1 | 5/2013 | Roeder et al. |
| 2015/0343181 A1 | 12/2015 | Bradway et al. |

FOREIGN PATENT DOCUMENTS

| | | |
|---|---|---|
| EP | 2724694 A2 | 4/2014 |
| WO | WO 97/21403 A1 | 6/1997 |
| WO | WO 2004/017868 A1 | 3/2004 |
| WO | WO 2004/089249 A1 | 10/2004 |
| WO | WO 2004/098388 A2 | 11/2004 |
| WO | WO 2006/007389 A1 | 1/2006 |

* cited by examiner

STENT GRAFT DELIVERY DEVICE PRE-LOADED WITH A SINGLE WIRE FOR DEVICE TRACKING AND CANNULATION

RELATED APPLICATIONS

This application claims priority to U.S. Provisional Application Ser. No. 62/128,705 filed on Mar. 5, 2015, which is incorporated by reference herein in its entirety.

TECHNICAL FIELD

This disclosure relates to introduction systems for the delivery and deployment of implantable medical devices. In particular, this invention relates to a stent graft delivery device or introducer that is pre-loaded with a guide wire that facilitates both device tracking and cannulation.

BACKGROUND

The introduction and deployment of a medical device such as a stent or stent graft into a patient is a well-known procedure. The introducer may include an external manipulation section or handle, an inner catheter that may accommodate a guide wire, a medical device carried by the inner catheter, a nose cone dilator at the proximal end of the inner catheter and a retractable outer sheath. The medical device is generally positioned at the proximal end of the introducer. During deployment, the implantable medical device is released from the introducer, first by retraction of the sheath and/or by the operation of other release mechanisms to facilitate expansion of the device in the body vessel.

Descending thoracic aortic aneurysms and dissections are often treated by placing a stent graft in the affected region of the vessel. In some procedures, the affected region (i.e., the location of an aneurysm or dissection) necessitates creating a seal with the stent graft at the location of a branch vessel extending from the main vessel, such as the left subclavian artery for example. In such cases, a fenestrated and/or branched graft may be used to maintain patency of both the main vessel and the branch vessel.

Accordingly, it may be desirable and advantageous to provide a stent graft delivery device or introducer that is pre-loaded with a single guide wire which can facilitate both the delivery of the stent graft to the desired location within a vessel as well as cannulation of one or more branch vessels.

SUMMARY

A nose cone dilator for a prosthesis delivery device is disclosed. In one example, the nose cone dilator comprises a proximal end having a proximal opening, a distal end, and a sidewall extending between the proximal and distal ends. A substantially straight internal lumen extends through the nose cone dilator between the proximal opening and the distal end. An opening is formed in the sidewall and an angled internal channel extends from the opening formed in the sidewall towards the proximal end. The angled internal channel extends to the substantially straight internal lumen and is in fluid communication with the substantially straight internal lumen.

A pre-loaded prosthesis delivery device is also disclosed. In one example, the delivery device comprises a delivery catheter having a proximal end and a prosthesis releasably secured to the proximal end of the delivery catheter. The prosthesis has a proximal end, a distal end, and a lumen extending there between. A nose cone extends from the proximal end of the delivery catheter. The nose cone comprises a proximal end having a proximal opening, a distal end, and a sidewall extending between the proximal and distal ends. A substantially straight internal lumen extends through the nose cone dilator between the proximal opening and the distal end. An opening is formed in the sidewall and an angled internal channel extends from the opening formed in the sidewall towards the proximal end. The angled internal channel extends to the substantially straight internal lumen and is in fluid communication with the substantially straight internal lumen. The delivery device further comprises a secondary catheter having a delivery configuration and a released configuration, wherein, in the delivery configuration the secondary catheter extends through at least a portion of the prosthesis lumen, into the opening formed in the sidewall of the nose cone and extends at least partially into the channel formed in the nose cone. In the released configuration, the secondary catheter is retracted distally out of the channel formed in the sidewall of the nose cone dilator.

A method of delivering a prosthesis is also disclosed. In one example, the method comprises the steps of tracking a prosthesis delivery device over a guide wire to a desired position within a main vessel. The delivery device comprises a delivery catheter having a tubular prosthesis releasably secured thereto and a nose cone extending from the proximal end of the delivery catheter. The nose cone comprises a proximal end having a proximal opening, a distal end, and a sidewall extending between the proximal and distal ends. A substantially straight internal lumen extends through the nose cone dilator between the proximal opening and the distal end. An opening is formed in the sidewall and an angled internal channel extends from the opening formed in the sidewall towards the proximal end. The angled internal channel extends to the substantially straight internal lumen and is in fluid communication with the substantially straight internal lumen. A secondary catheter extends through at least a portion of the tubular prosthesis and extends at least partially into the internal channel formed in the nose cone. The method further comprises distally retracting the secondary catheter to release it from the internal channel and manipulating the secondary catheter to cannulate a branch vessel extending from the main vessel.

BRIEF DESCRIPTIONS OF THE DRAWINGS

FIG. 11 shows another example of a variable diameter tip in a reduced-diameter configuration with a single resilient elongated member extending there through.

FIG. 11A shows another example of a variable diameter tip in a reduced-diameter configuration with two resilient elongated members extending there through.

DETAILED DESCRIPTION

The present disclosure relates to a delivery device or introducer for delivering a radially expandable stent graft within a human or animal body for repair of damaged vessels, ducts, or other physiological pathways and systems. In the present disclosure, the term "proximal" refers to a direction that is away from a physician during a medical procedure, while the term "distal" refers to a direction that is closest to the physician during the procedure. In addition, like reference numbers throughout the various drawings designate similar structure.

Figure 1:
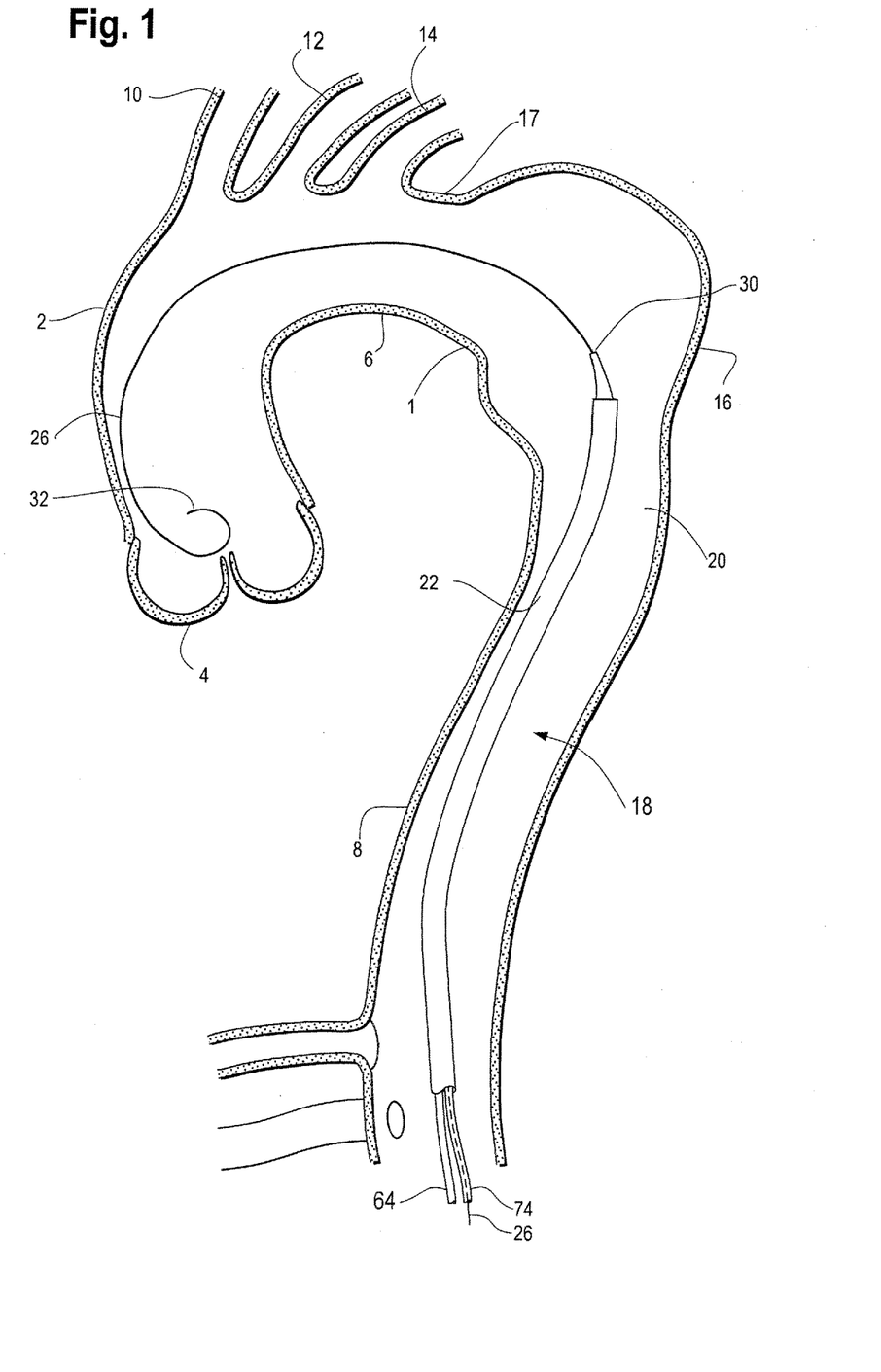
FIG. 1 shows an example of an introducer located within a vessel.

FIG. 1 shows an example of an introducer that has been tracked over a guide wire to a desired location within a curved vessel. In FIG. 1, the curved vessel 1 is the thoracic aorta. The thoracic aorta includes the ascending aorta 2 extending from the aortic valve 4 of the heart of the patient, the thoracic arch 6 and the descending aorta 8. Three branch arteries extend from the main artery (the thoracic arch 6) including the innominate artery 10, the left carotid artery 12 and the left subclavian artery 14. As shown, an aneurysm 16 has developed just distal of the left subclavian artery 14. The space 17 between the most proximal portion of the aneurysm 16 and the left subclavian artery 14 may, in some cases, be relatively short as shown in FIG. 1, and in other cases the space may be longer. Depending on the patient's unique anatomy and the location of the aneurysm 16, it may be necessary to extend the proximal end of a stent graft deployed in the vessel lumen 20 to an area or location that is proximal of the left subclavian artery 14 but distal to the left carotid artery 12. In doing so, blockage of some or all of the left subclavian artery 14 by the body of the stent graft may result. Accordingly, it may be advantageous to provide an introducer that is pre-loaded with a guide wire and a stent graft to maintain and/or restore patency to those vessels. As described herein, the stent graft carried on the introducer is preferably pre-cannulated with the guide wire. Thus, a single guide wire facilitates tracking of the introducer within a vessel and cannulation of the stent graft carried on the introducer while also allowing cannulation of one or more of the branch vessels during use.

As partially shown in FIG. 1, an introducer 18 has been advanced into the lumen 20 of the vessel 1. In one example, the introducer 18 includes a retractable or removable sheath 22 and a secondary catheter 74. One or more guide wires 26 may extend through the lumen of the secondary catheter 74. The guide wire 26 may first be introduced into the vessel 1 and the introducer 18 then tracked over the guide wire 26 to a desired position within the vessel. Alternatively, the guide wire 26 and/or the secondary catheter 74 may be pre-loaded within the introducer, meaning that the guide wire 26, the secondary catheter 74, or both, are loaded or assembled onto or are otherwise a part of the introducer 18 before use and before the introducer is tracked into and through a vessel. Thus, when the guide wire 26 and secondary catheter 74 are pre-loaded, they are thereby inserted into a vessel simultaneously with the introducer 18. In yet a further example, the guide wire 26 may be inserted through the introducer 18 (through secondary catheter 74) and into the vessel 1 after the introducer has been positioned in the vessel 1. The introducer 18 also includes a nose cone dilator 28 extending proximally from the proximal end of the delivery catheter 66. The nose cone dilator 28 may be tapered and/or flexible to present an atraumatic tip.

As shown, the guide wire 26 extends through the secondary catheter 74 of the introducer 18, through at least a portion of the nose cone dilator 28 and has been extended further proximally to extend from the tip 30 of the nose cone dilator 28. Guide wire 26 may facilitate the delivery, placement, adjustment and movement of the delivery device 18 within the vessel 1. The proximal tip 32 of the guide wire 26 may have a curved (pig-tailed end) atraumatic tip so as not to pierce or damage the walls of the vessel lumen 20 and/or the aortic valve 4. The introducer 18 can be substantially straight or it may have a curved configuration imparted at its proximal end as described in U.S. Pat. No. 8,394,135, which is incorporated by reference herein. The nose cone dilator 28 also may be straight or curved, as shown in FIGS. 9 and 10 of U.S. Publication Application No. 2011/0125244 and in U.S. Pat. No. 7,611,529, which are both incorporated by reference herein. Prior to and during delivery of a prosthesis, such as a stent graft 34, the sheath 22 extends proximally to cover the stent graft 34 carried on introducer 18 to hold the stent graft in a radially inwardly contracted delivery configuration. The sheath 22 may extend proximally to cover at least the distal end of the nose cone dilator 28 as illustrated in FIG. 1.

Figure 2:
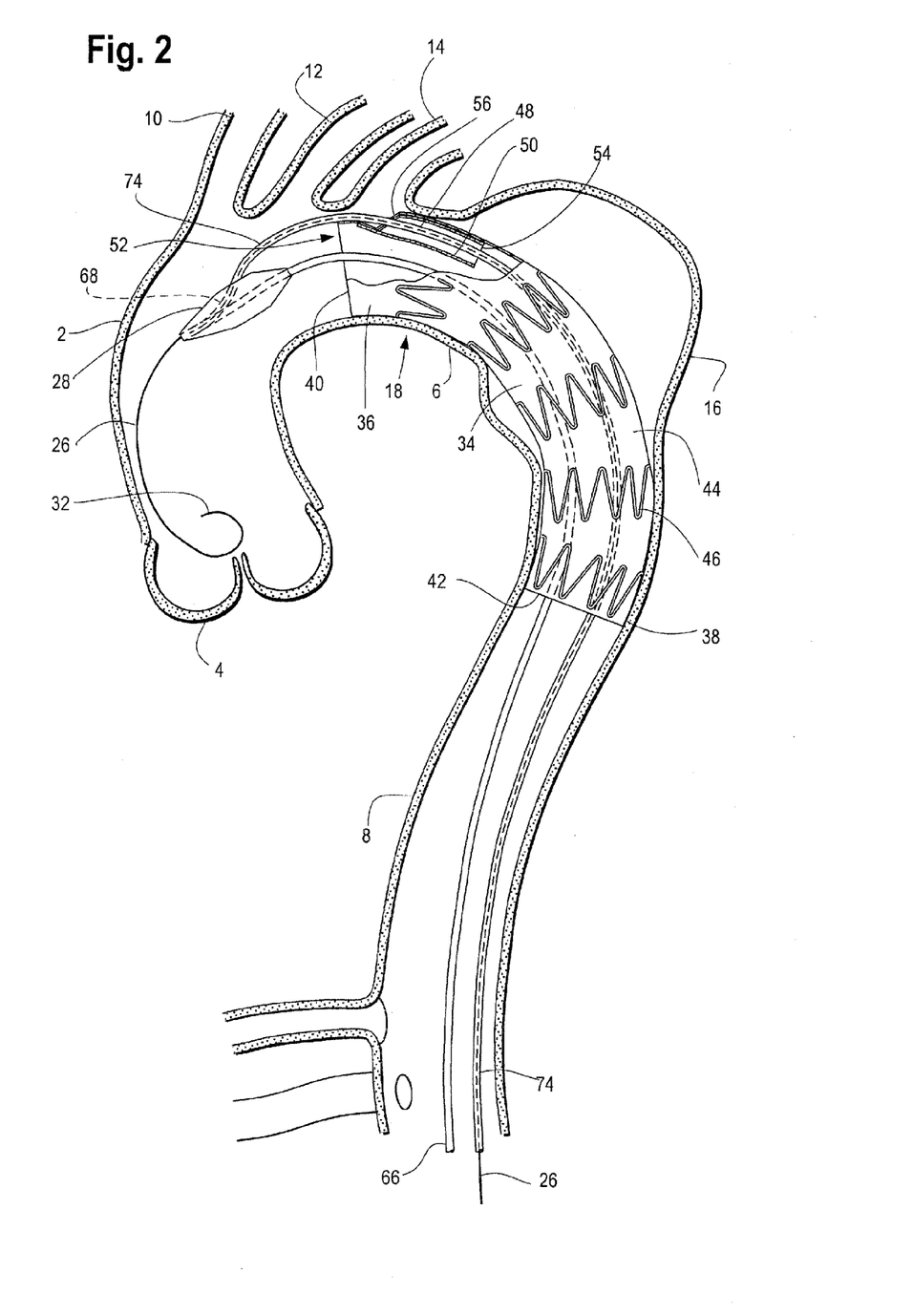
FIG. 2 shows an example of an introducer located within a vessel and a stent graft deployed therein.

FIG. 1 shows an example of an introducer 18 tracked over guide wire 26 to a location within a vessel 1, with the stent graft 34 still covered and held in a radially inwardly contracted delivery configuration by sheath 22. FIG. 2 shows the introducer of FIG. 1 within the vessel 1 after the sheath 22 has been distally retraced allowing the stent graft 34 to deploy from the introducer 18 and become expanded within the vessel 1 at the site of aneurysm 16. As shown, the stent graft 34 has a proximal end 36, a distal end 38, a proximal opening 40, a distal opening 42 and a tubular body 44 extending between the proximal 36 and distal 38 ends to define a graft lumen 52. The stent graft 34 may be a generally singular tube-like configuration with an internal side branch 48 extending within the lumen 52 of the graft body 44 as illustrated in FIG. 2, although other configurations are also contemplated. For example, the stent graft 34 may be a fenestrated stent graft (wherein one or more openings or fenestrations are formed in the graft body 44) and/or a bifurcated stent graft (with first and second legs extending from the main graft body).

A series of stents 46 may be attached to the graft body 44 and extend along all of, or at least part of, the length of the stent graft 34. An exposed anchoring stent (not shown) with one or more barbs for attaching the stent graft to a vessel wall may extend from the proximal end 36 of the graft body 44 as described in US Publication Application No. 2012/0277848, which is incorporated by reference herein. The stents 46 may be sutured to the graft material or held to the graft material in other known ways. The series of body stents 46 may be internal or external to the graft body 46, or both. For example, one of the stents 46 near the proximal end 36 and/or the distal end 38 of the stent graft 34 may be an internal sealing stent while the remaining body stents 46 are external to the graft body 44. Any one or more of the stents 46 may be provided with barbs that extend from the stent inside the tubular graft body and through the graft material to engage the vessel wall. Radiopaque markers (not shown) may be placed on various parts of the stent graft 34 to aid the user in positioning the stent graft during deployment.

Stents 46 may be zig-zag shaped as shown in FIG. 2, although other stent configurations are known and may be used alone or in combination with the zig-zag stents 46 and/or have other configurations as known in the art. The stents may be constructed of a self-expanding shape memory material, such as Nitinol, or they may be balloon expandable, or a combination of both depending on the particular characteristics desired of the stent graft.

As shown in FIG. 2, stent graft 34 is a branched stent graft that has been deployed in the aorta 1, having a series of self-expanding stents 46 extending along the length of the graft body 44. In this example, the branch 48 is an internal branch. In other words, the body 50 of the branch 48 extends within the lumen 52 of the stent graft 34. The branch 48 has a proximal end that extends from an aperture 56 formed in the sidewall of the graft body 44 and has a distal open end 54 that opens into lumen 52 of the stent graft 34.

Figure 3:
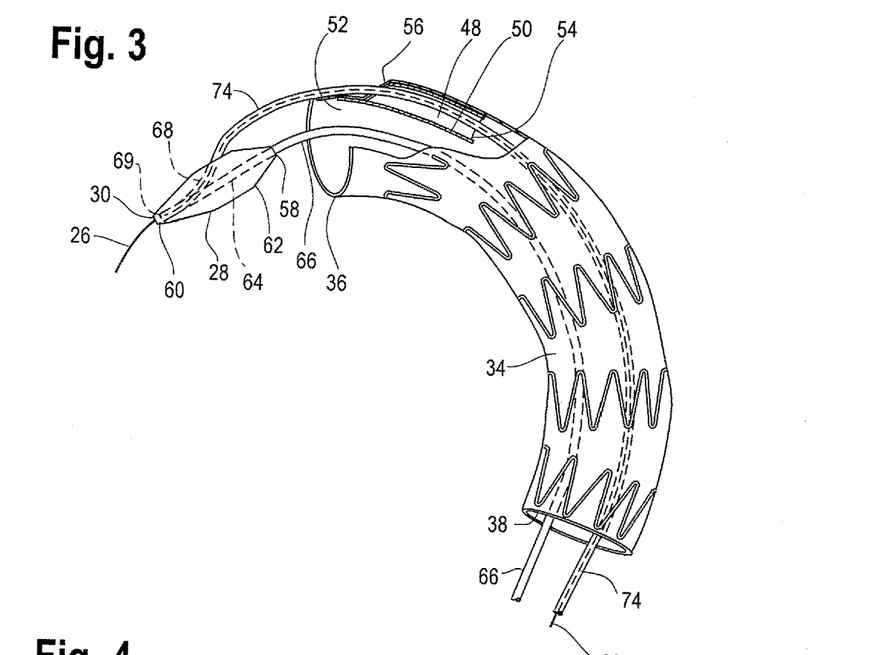
FIG. 3 shows the proximal end of the introducer of FIG. 2 with one example of a deployed branched stent graft having a catheter and a guide wire extending proximally through a portion of the stent graft and into a channel formed in the nose cone dilator.

FIG. 3 illustrates an introducer 18 with one example of a nose cone dilator 28 and a fully deployed stent graft 34. As shown in FIG. 3, nose cone dilator 28 has a distal end 58 and a proximal end 60 and a side wall 62 extending between the proximal and distal ends. Nose cone dilator 28 may have a straight or substantially straight lumen 64 formed within and extending the length of the nose cone dilator 28 between the distal end 58 and proximal end 60. The straight lumen 64 may be configured to receive one or more guide wires and/or catheters there through. In one example, straight lumen 64 receives at least a proximal end of delivery catheter 66 but does not receive a guide wire.

Figure 4:
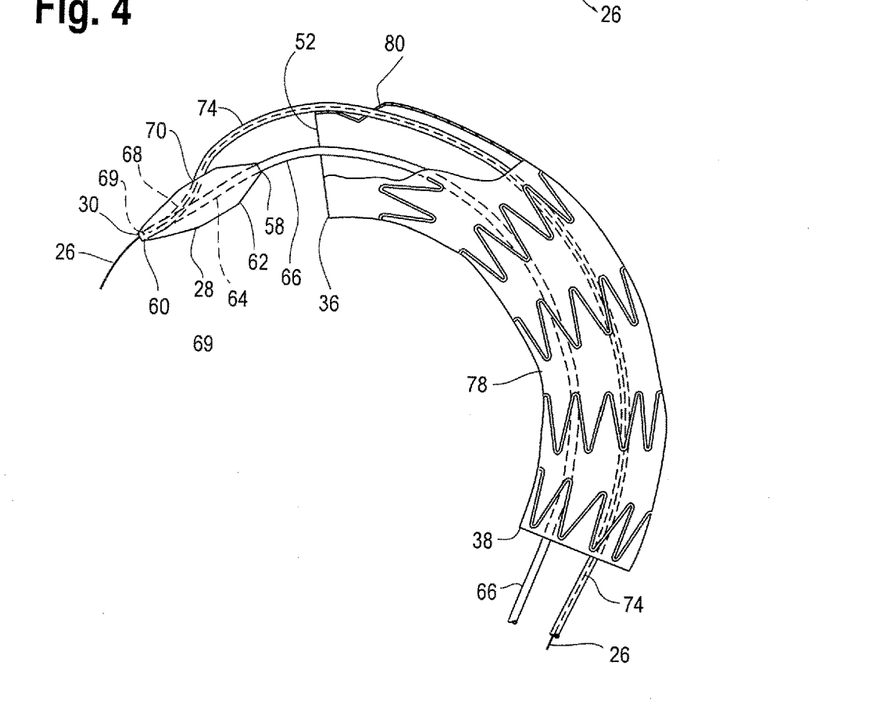
FIG. 4 shows the proximal end of an introducer with one example of a deployed fenestrated stent graft having a catheter and a guide wire extending proximally through a portion of the stent graft and into a channel formed in the nose cone dilator.

Nose cone dilator 28 may also have a channel 68 formed within and extending proximally through a portion of the length of the nose cone dilator 28 from aperture 70 formed in the side wall 62 to the proximal end of the nose cone dilator 28. In one example, the channel 68 extends proximally from the aperture 70 and may converge with the straight lumen 64. The channel 68 may be straight or it may be at least partially curved and extend from the proximal end 60 of the nose cone dilator 28 (or from where it is converged with straight lumen 64) and exit from the nose cone through the side wall 62 of the nose cone dilator at aperture 70, as shown in FIG. 4. In one example, channel 68 may extend substantially longitudinally for a distance (i.e., substantially parallel to straight lumen 64) and then curve at its distal end to exit the side wall 62 of the nose cone dilator 28 through aperture 70 at a location approximately midway between the proximal end 60 and distal end 58 of the nose cone dilator 28 as shown in FIGS. 3 and 4. However, the curved channel may exit the nose cone dilator 28 either closer to the proximal end 60 or closer to the distal end 58. In another example, the channel 68 may be straight or substantially straight or it may have a curve imparted to its entire length or may have a helical shape imparted to it.

In an alternative example (not shown), the channel 68 may be in the form of an elongated opening or slot extending from the aperture 70 formed in the side wall 62 of the nose cone dilator 28 towards the proximal end 60. The channel or slot may extend partially or, alternatively, extend all the way to the proximal end 60 of the nose cone dilator 28. In yet a further example, a groove (not shown) formed in the surface of the nose cone side wall 62 may be used in place of the curved channel 68. The channel 68 (and/or slot or groove) may extend partially and/or fully in a proximal direction from a point of origination (such as aperture 70 and/or the beginning of the groove) towards the proximal end 60 of the nose cone. The channel 68 (or slot or groove) is preferably shaped and configured to receive at least a portion of the guide wire 26 and/or the secondary catheter 74 therein.

In another example, either alone or in combination with the above, a trigger wire (not shown) may also be provided to constrain the proximal tip of the guide wire 26 and/or the secondary catheter 74 against or within the nose cone dilator 28. More specifically, one or more trigger wires may be used to retain the guide wire 26 and/or the secondary catheter 74 within the curved channel 68 (or within the above-described alternatives, including the elongated opening, slot or groove formed in the nose cone dilator 28). The one or more trigger wires may pass over the secondary catheter 74 (and/or guide wire 26 extending through the secondary catheter 74) at one or multiple points along its length and secure it to the nose cone dilator 28. Thus, when the trigger wire(s) is removed, the secondary catheter 74 (and guide wire 26) are freed from the nose cone dilator 28 and can then be manipulated by the user to make any necessary exchanges, including, but not limited to cannulating a side vessel (such as the left subclavian artery) extending from the aorta 1. When only trigger wire(s) are used to secure the secondary catheter 74 to the nose cone dilator 28 (and the secondary catheter 74 is not constrained within the curved channel 68 or above-described slot), it may not be necessary to distally retract the secondary catheter 74 to free it from a constrained configuration within the channel 68. Instead, removal of the trigger wire(s) will free the secondary catheter 74 from the nose cone dilator 28 so that it is available for further manipulation by the user.

Secondary catheter 74 can be preloaded on the introducer 18 with guide wire 26 extending there through. Alternatively, guide wire 26 may first be inserted into the vasculature and the introducer 18 then tracked over the guide wire 26, through secondary catheter 74, and into position within the vessel. In a non-limiting example, one procedure for introducing the introducer 18 into a patient is by means of the well-known Seldinger technique, in which a guide wire 26 is first inserted percutaneously into a patient's vasculature via a needle (not shown). The introducer 18 is inserted percutaneously and endoluminally into the patient, over the guide wire 26, which acts to guide the introducer 18 through the vasculature up to the treatment site.

In one example, the straight lumen 64 and curved channel 68 create a "Y" shape within the nose cone dilator 28. In other words, as shown generally in FIGS. 5 and 6, the straight lumen 64 lies in a relatively straight line from the proximal end 60 to the distal end 58 of the nose cone dilator 28 and the curved channel 68 intersects or otherwise converges with the straight lumen 64 at some point between the proximal end 60 to the distal end 58 of the nose cone dilator 28 to generally form a "Y" configuration. In one example, the curved channel 68 intersects or converges with the straight lumen 64 about half way between the proximal end 60 to the distal end 58 of the nose cone dilator 28, although, the channel 68 may intersect the straight lumen 64 closer to the proximal end 60 and/or closer to the distal end 58 of the nose cone dilator 28.

As shown in FIGS. 3 and 4, the stent graft 34 carried by the introducer 18 can be pre-loaded with the guide wire 26. In one example, the guide wire 26 can extend proximally through the lumen 52 of the graft body 44, into the distal end 54 of the internal branch 48 and exit out of the branch 48 at proximal branch opening 56. The proximal tip 32 of the guide wire 26 can extend through channel 68 of the nose cone dilator 28 and into the proximal end 60 of the nose cone dilator 28. As shown in FIGS. 1 and 2, the guide wire 26 can, in use, be proximally advanced all the way out of the proximal end 60 of the nose cone dilator 28.

Secondary catheter 74 is coaxial with at least a portion of the guide wire 26. In one example, the secondary catheter 74 is also pre-loaded within the introducer 18, such that the secondary catheter 74 extends coaxially with and proximally over the guide wire 26, through the lumen 52 of the graft body 44, into the distal end 54 of the internal branch 48. The secondary catheter 74 then exits out of the branch 48 at proximal branch opening 56. As FIG. 2 shows, the proximal end 76 of the secondary catheter 74 can be tucked into and held within the curved channel 68 of the nose cone dilator 28. As shown in FIGS. 3 and 4 (and shown in greater detail in FIG. 7) the curved channel 68 (168 of FIG. 7) may have a substantially constant inner diameter along its length, and near the proximal end 60 of the nose cone dilator 28, the inner diameter of the channel 68 becomes narrowed at point 69. In this way, the secondary catheter 74 (174) can advance proximally through the channel 68 (168) to the proximal end 60 of the nose cone dilator 28 but it cannot advance through the narrowed inner diameter portion 69 of the channel 68. While the guide wire 26 (126) may pass through the narrowed diameter portion 69 of the channel 68, the secondary catheter 74 cannot pass through this narrowed diameter portion 69 of the channel 68 and is therefore prevented from extending proximally out of the proximal tip 30 (130) of the nose cone dilator 28.

As shown partially in FIG. 1, the delivery catheter 66 may extend proximally from an external manipulation handle section or distal end of the introducer 18 (identified as reference number 100 in FIG. 8) through the lumen 52 of the graft body 44 and into the straight lumen 64 of the nose cone dilator 28 to secure the nose cone dilator 28 to the proximal end of the delivery catheter 66. The delivery catheter 66 may terminate within the lumen 64 near the distal end 58 of the nose cone dilator 28, or alternatively, the delivery catheter 66 may extend further into the lumen 64 and terminate at a point closer to the proximal end 60 of the nose cone dilator 28.

As shown in FIGS. 1 and 2, the guide wire 26 advantageously serves as a means to track the introducer 18 to a desired location within the vessel 1 while also pre-cannulating the internal branch 48 of the stent graft 34 with a single wire 26. In other words, introduction of the introducer and cannulation of the internal graft branch 48 may be combined through the use of a single guide wire 26, and this same guide wire may then be further manipulated during use to cannulate one or more branch vessels extending from the main vessel.

In one example, as FIG. 1 shows, a guide wire 26 can be inserted percutaneously and advanced proximally through a vessel 1. Next, the introducer 18 containing a prosthesis (such as stent graft 34) held in a radially compressed delivery configuration under a sheath 22, can be advanced over the guide wire 26. When the prosthesis is in a deployment position within a vessel lumen 52, the sheath 22 can be withdrawn and the stent graft 34 can be at least partially deployed by one or more known methods. For example, following sheath retraction, one or more trigger wires or diameter reducing ties (not shown) at the proximal end 36 of the stent graft 34 and/or the distal end 38 of the stent graft, or both ends, can be removed allowing the stent graft 34 to radially outwardly expand and deploy from the introducer 18.

FIG. 4 shows an example of the proximal end of an introducer 18 with another example of a stent graft 78 carried on the introducer 18. The stent graft shown in FIG. 4 is a fenestrated stent graft 78 that has been deployed within a vessel 1. Fenestrated stent graft 78 has at least one fenestration or opening 80 formed in the sidewall of the graft body 44.

A guide wire 26 can be threaded proximally through the lumen 52 of the graft 78 and extended out of the lumen 52 through the fenestration 80. The proximal tip 32 of the guide wire 26 can then be threaded into and through the curved channel 68 of the nose cone dilator 28. The guide wire 26 can advance into the proximal end 60 of the nose cone dilator 28 and be further advanced proximally all the way out of the proximal end 60 of the nose cone dilator 28.

As also shown in FIG. 4, the secondary catheter 74 is coaxial with at least a portion of the guide wire 26. In one example, the secondary catheter 74 is pre-loaded within the introducer 18, such that the secondary catheter 74 extends proximally over the guide wire 26 and through the lumen 52 of the graft body 44, and exits out of the graft lumen 52 through fenestration 80. The proximal end 76 of the secondary catheter 74 can be tucked into and held within the curved channel 68 of the nose cone dilator 28. The secondary catheter 74 can advance towards the proximal end 60 of the nose cone dilator 28 but it cannot advance all the way out of the proximal end 60 of the nose cone dilator 28 due to the narrowed inner diameter portion 69 of the channel 68. Like FIGS. 1-3, the guide wire 26 of FIGS. 4 and 6 also advantageously serves as a means to track the introducer 18 to a desired location within the vessel while also pre-cannulating the fenestration 80 with a single wire 26. In other words, the stent graft 78 is pre-cannulated within the introducer by the guide wire 26 (i.e., the wire extends through the graft lumen and fenestration 80), and in addition, the guide wire allows the introducer to be tracked into place within a vessel while also allowing the wire to be manipulated in use to cannulate a branch vessel, as described below.

Figures 5, 6:
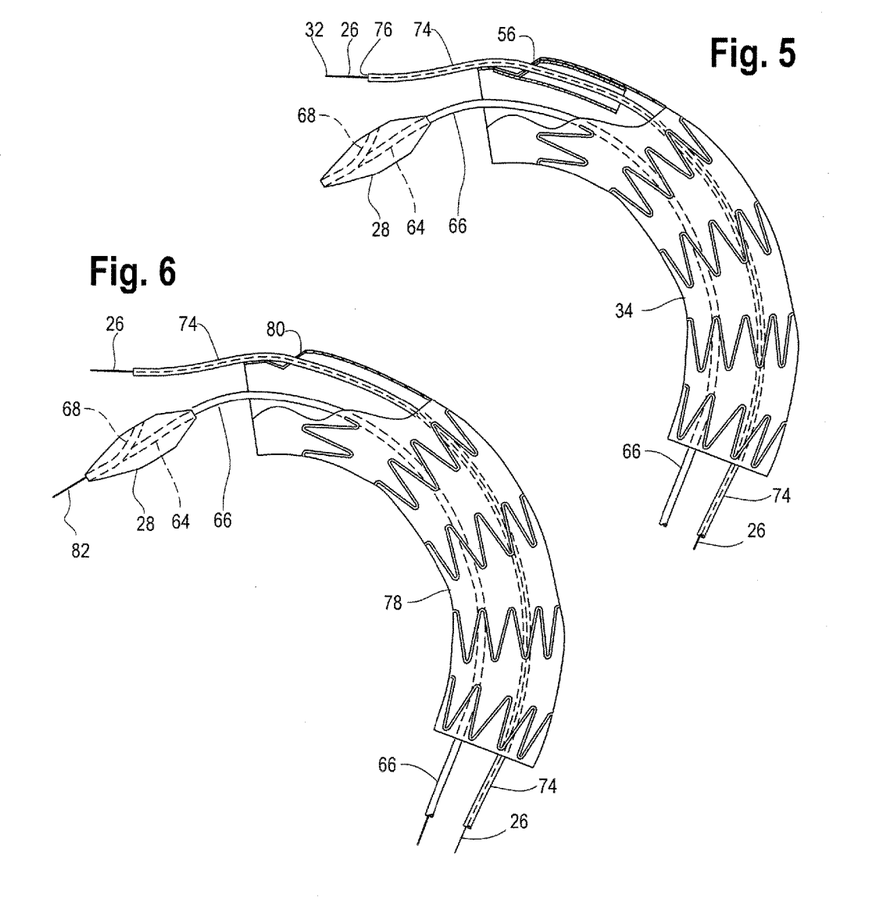
FIG. 5 shows the introducer of FIG. 3 where the guide wire and catheter have been distally retracted out of the channel formed in the nose cone dilator.
FIG. 6 shows the introducer of FIG. 4 where a guide wire and catheter have been retracted out of a channel formed in the nose cone dilator and a secondary guide wire remains in a straight lumen of the nose cone dilator.

FIGS. 5 and 6 show the guide wire 26 and secondary catheter 74 retracted partially distally. The proximal tip 32 of the guide wire 26 has been withdrawn distally from the nose cone dilator 28. In addition, the secondary catheter 74 has been retracted distally so that it is no longer constrained within the channel 68 of the nose cone dilator 28. In this configuration, the user is free to manipulate the guide wire 26 and/or the secondary catheter 74 to make any necessary exchanges, such as, for example, to cannulate one or more of the branch vessels (such as the left subclavian artery, left carotid and/or innominate artery) extending from the main vessel 1 as described generally below.

In one non-limiting example of use, the introducer 18 may be tracked over guide wire 26 to a desired stent graft position within a vessel 1 as shown in FIG. 1. The sheath 22 can then be distally retracted to expose the stent graft 34 (or stent graft 78 of FIGS. 4-6) and any trigger wires or diameter reducing ties removed to allow the stent graft to release from the introducer 18 and deploy within the vessel 1. At this time, it may be desirable to cannulate a branch vessel, such as the left subclavian artery 14, left carotid artery 12 and/or innominate artery 10, extending from the main vessel 1. To do so, the user may distally retract the guide wire 26 and secondary catheter 74. This retraction will free guide wire 26 and secondary catheter 74 from the curved channel 68 in the nose cone dilator 28 as shown in FIGS. 5 and 6. When the proximal end 76 of secondary catheter 74 is freed from the channel 68, the guide wire 26 may then be manipulated by the user to cannulate a desired branch vessel. For example, the user may advance the guide wire 26 proximally and extend it into, and thereby cannulate the left subclavian artery 14. If necessary or desired, a secondary stent graft, such as an extension stent graft (not shown) loaded on to a secondary introducer (not shown) may be tracked over the guide wire 26 and into the cannulated branch vessel to deliver and deploy the extension branch therein, thus restoring and/or maintaining patency to the branch vessel.

FIG. 6 shows another example of an introducer 18 with a stent graft 78 deployed from the proximal end of the introducer 18. The guide wire 26 and secondary catheter 74 have been retracted distally out of the channel 68 in the nose cone dilator 28. In one non-limiting example shown in FIG. 6, the nose cone dilator 28 may have a straight lumen 64 extending between the proximal end 60 and distal end 58, configured to receive a secondary guide wire 82 there through. If desired, the secondary guide wire 82 can be advanced through the straight lumen 64 and be extended out of the proximal end 60 of the nose cone dilator 28. In doing so, the nose cone dilator 28 will still have a guide wire 82 extending there through to reinforce and constrain the positioning of the nose cone dilator 28 within the vessel lumen, while also maintaining a pathway for the introducer to be tracked over, even after guide wire 26 and/or secondary catheter 74 has been partially or fully withdrawn from the body.

Figure 7:
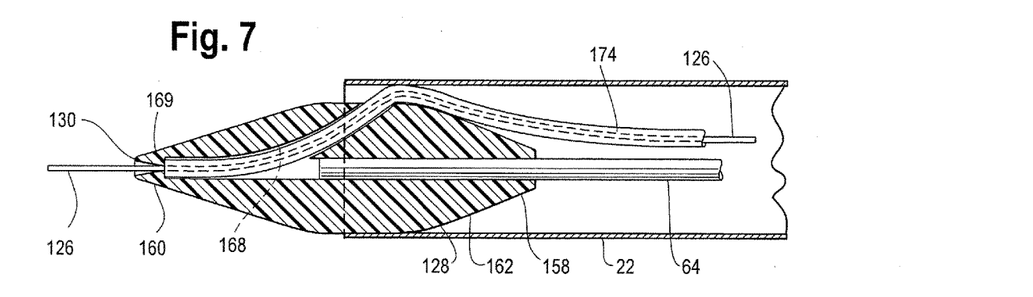
FIG. 7 shows an enlarged view of a nose cone dilator with a catheter and guide wire extending through a curved channel and a straight lumen extending through the nose cone, the nose cone and catheter being covered by a retractable sheath.

FIG. 7 shows an enlarged view of the nose cone dilator 128 with a channel or lumen 168 extending there through. As previously described, the nose cone dilator 128 has a channel 168 that extends from the proximal end 160 of the nose cone dilator 128 and terminates at aperture 170 formed in a side wall 162 of the nose cone dilator. Channel 168 can be configured to receive a guide wire 126 and a secondary catheter 174 therein. As shown in FIG. 7, the channel 168 may have a substantially constant inner diameter along its length, and near the proximal end of the nose cone dilator 128, the inner diameter of the channel 168 becomes narrowed at location 169. In this way, the secondary catheter 174 can advance proximally through the channel 168 to the proximal end 160 of the nose cone dilator 128 but it cannot advance through the narrowed inner diameter portion 169 of the channel 168. While the guide wire 126 may pass through the narrowed diameter portion 169 of the channel 168, the secondary catheter cannot pass through this narrowed diameter portion 169 of the channel 168 and is therefore prevented from extending proximally out of the proximal tip 130 of the nose cone dilator 128.

Variable Diameter Dilator Tip

Figure 8:
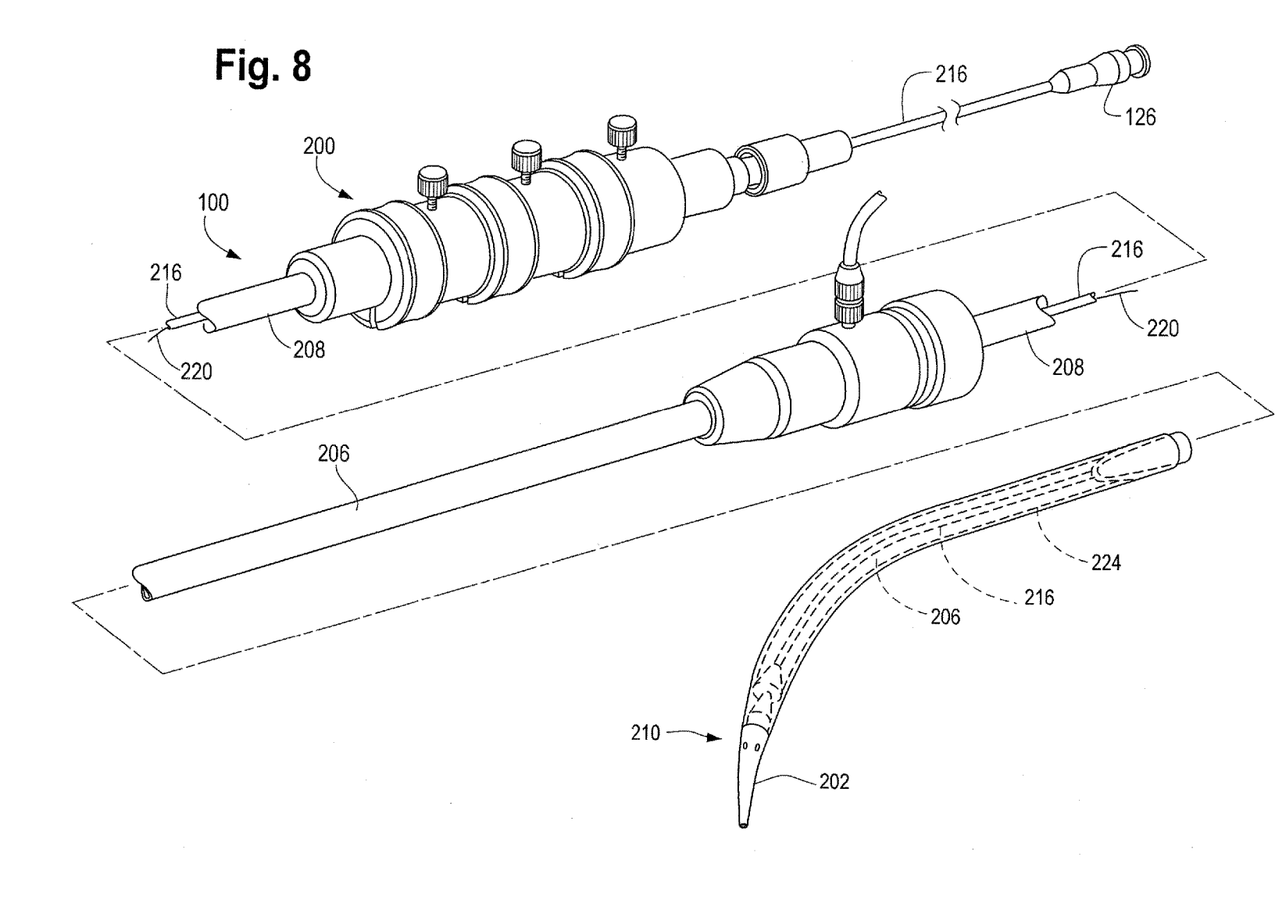
FIG. 8 shows one example of a conventional introducer.

FIG. 8 shows an example of a proximal end portion of a conventional introducer assembly 200. Introducer assembly 200 has a dilator tip 202 at its proximal end 210 and an external manipulation section or handle at the distal end 100. A flexible delivery catheter 216 extends from a location distal to the handle 100 to the dilator tip 202. Although this introducer 200 can be used in any area of the vasculature, it is described here as being used in the aortic arch.

Figure 9:
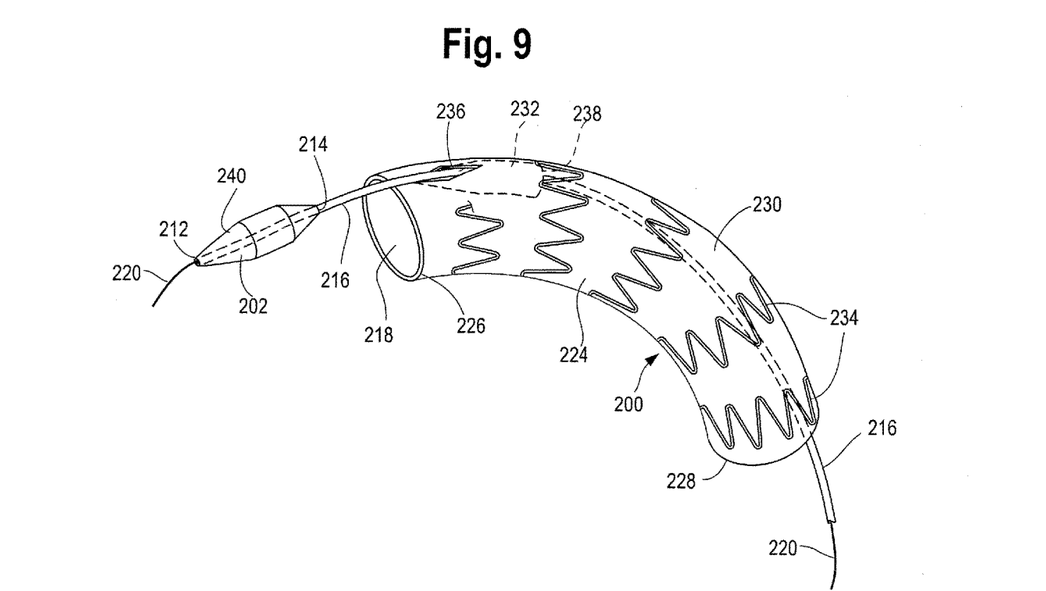
FIG. 9 shows an introducer with a deployed branched stent graft and a variable diameter dilator tip in an expanded-diameter configuration.

As FIG. 8 and FIG. 9 shows, an implantable medical device, such as a stent graft 224, is carried on the delivery catheter 216 at the proximal end. A retractable introducer sheath 206 retains the stent graft 224 in a radially inwardly contracted delivery configuration on the delivery catheter 216 and can be retracted during deployment. The introducer 200 typically includes a pusher member 208 coaxial with the delivery catheter 216. The pusher member 208 extends proximally from the distal end or handle portion of the introducer and terminates at a location distal to the stent graft 224. In one example, the introducer assembly 200 includes a guide wire 220 which passes through the delivery catheter 216 and the dilator tip 202. In use, the introducer 200 can be tracked over the guide wire 220 to a desired location within the vasculature during the delivery and deployment procedure.

The delivery catheter 216 may extend proximally through the lumen 218 of the stent graft to the dilator tip 202. In another example, where a fenestrated stent graft is used (such as the fenestrated stent graft 44 shown in FIG. 4), the delivery catheter 216 may extend into the distal end of the stent graft 224, then outwardly through the fenestration 80 formed in the side wall of the graft and continue proximally to the dilator tip 202. In yet another example, where a branched stent graft is used as shown in FIG. 9), the delivery catheter 216 may extend proximally into the distal end 228 of the stent graft, through the lumen of the internal graft branch 232 and continue out of the branch to the dilator tip 202.

The dilator tip 202 is preferably tapered and smooth, thereby facilitating atraumatic tracking and guiding of the introducer 200 through tortuous vasculature to a desired location within a vessel. In one example, the dilator tip 202 has a variable diameter. For example, the dilator tip 202 may be radially outwardly expanded, either partially or fully, during delivery of the stent graft. More specifically, when dilation is required, such as during insertion of the introducer 200 into a patient, the tip may be partially expanded, or alternatively, fully expanded, so that the outer diameter of the dilator tip 202 is at its maximum size. The introducer 200 may then be tracked to its desired position within the vessel. After graft deployment, the dilator tip 202 may be reduced in diameter to a smaller, radially inwardly contracted configuration. With the outer diameter of the dilator tip 202 reduced, the tip 202 can be retracted distally through the stent graft 224 for removal from the vessel.

Figure 10:
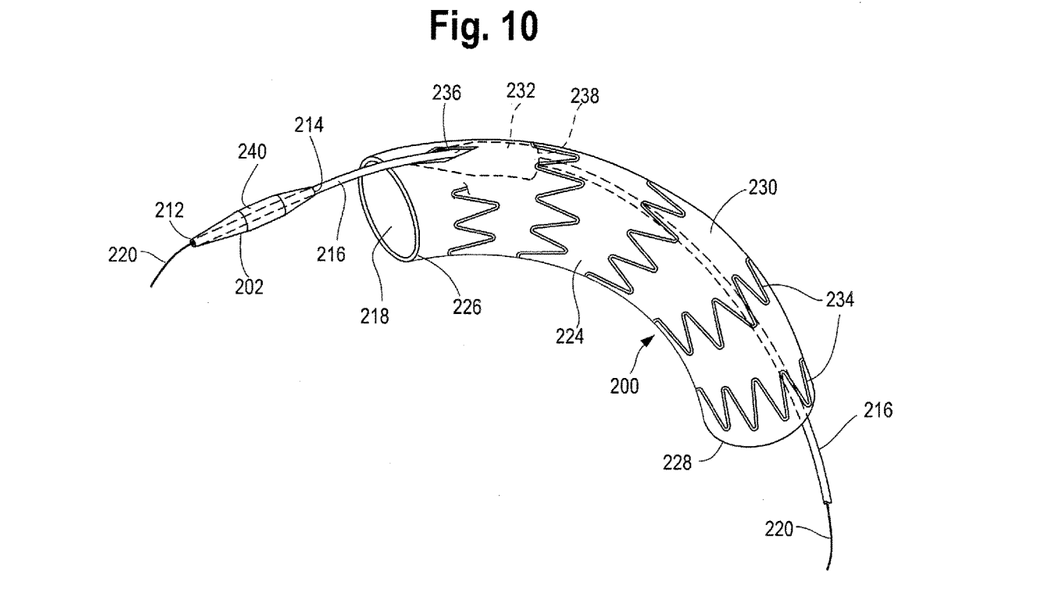
FIG. 10 shows the introducer of FIG. 9 with a deployed branched stent graft and a variable diameter dilator tip in a reduced-diameter configuration.

In another example, where the delivery catheter 216 extends through a fenestration and/or side branch of the stent graft (such as, for example, the fenestration 80 formed in the side wall of the graft body 44 of FIG. 4 and/or the branch 232 of the stent graft body 230 shown in FIG. 9), the reduction of the diameter of the dilator tip 202 advantageously facilitates retraction and withdrawal of the tip 202 through the lumen 218 of the stent graft body 230, through the fenestration and/or through the graft side branch 232, while reducing the risk of the tip 202 snagging on any portion of the stent graft (including the fenestration and/or the graft side branch 232) or from snagging on any other portion of the introducer 200 during retraction of the dilator tip 202 out of the body. If desired, the guide wire 220 may be left in place within the main vessel 1, such as for further manipulation by the user to cannulate one or more branch vessels 10, 12 and/or 14, and retracted at a later time during a procedure FIG. 9 shows an introducer 200 with a deployed branched stent graft 224 and a variable diameter dilator tip 202 in a radially outwardly expanded-diameter configuration. FIG. 10 shows the introducer 200 of FIG. 9 with a deployed branched stent graft 224 and a variable diameter dilator tip 202 in a radially inwardly contracted or reduced-diameter configuration. The dilator tip 202 shown in FIGS. 9 and 10 may be a balloon-like resilient element constructed of a material having radially expandable and contractible properties. For example, the dilator tip 202 may be formed of polyurethane, nylon, PEBAX® (Polyether block amide), PVC, and/or other resilient materials or a combination thereof. The tip 202 may have a substantially conical shape, spherical shape or onion shape to facilitate atraumatic insertion in a body lumen. The diameter of the outer surface of the dilator tip 202 may vary along its longitudinal length. For example, the tip 202 may have a proximal taper and/or a distal taper, with the center portion of the tip 202 having a greater diameter than the proximal and distal tapered portions when the tip 202 is in both the expanded condition and the contracted condition. A lumen extends through the dilator tip 202 between its proximal end 212 and distal end 214. The guide wire 220 extends proximally through the lumen of the delivery catheter 216 and can be extended through the lumen of the dilator tip 202.

FIG. 9 illustrates the proximal end of an introducer 200 with a branched stent graft 224 in a radially outwardly deployed configuration. The stent graft 224 may have a proximal end 226, distal end 228 and a tubular graft body 230 extending there between. One or more stents 234 may be attached to the tubular graft body 230. Branched stent graft 224 may have a proximal branch opening or aperture 236 located near the proximal end 226 of the stent graft 224. An internal graft branch 232 extends distally from the branch opening 236 within the lumen 218 of the stent graft 224. The dilator tip 202 and delivery catheter 216 may extend through the lumen 218 of branched stent graft 224. In one example shown in FIG. 9, the delivery catheter 216 and dilator tip 202 extend proximally through the lumen 218 of the stent graft 224, into the distal opening 238 of the branched stent graft 224 and exits the graft 224 through the proximal branch opening 236. Although not shown, in another example, a fenestrated stent graft can be used instead of a branched stent graft. In one example, the cannula assembly would pass out of a fenestration instead of through the branch opening.

As mentioned above, the dilator tip 202 is moveable between a radially outwardly expanded-diameter configuration (FIG. 9) and a radially inwardly reduced-diameter configuration (FIG. 10). During insertion of the introducer 200 into a patient, dilator tip 202 can be in an at least partially expanded configuration. Once a user has tracked the introducer 200 into a desired location and deployed the stent graft 224, the outer diameter of the dilator tip 202 may be reduced to a smaller diameter contracted configuration. The dilator tip 202 and delivery catheter 216 may then be withdrawn from the patient by pulling distally on the cannula, such as by retracting handle 100.

Several different mechanisms can be used to control the variable diameter of the dilator tip 202. In one example, the dilator tip 202 has an inner cavity which can be filled with fluid, gel and/or gas as shown and described in U.S. Publication Application No. 2012/0109056, which is incorporated by reference herein. Another mechanism to control the diameter of the dilator tip 202 is by mechanical means. In one example, a flexible outer surface 240 covers an expandable structure such as, for example, a series of members, fingers, cages, mesh and the like which can be mechanically expanded and contracted. As the structure is expanded and contracted, the flexible outer surface 240 radially expands and contracts along with it, thus providing the user with control over the diameter of the dilator tip 202.

Figure 11:
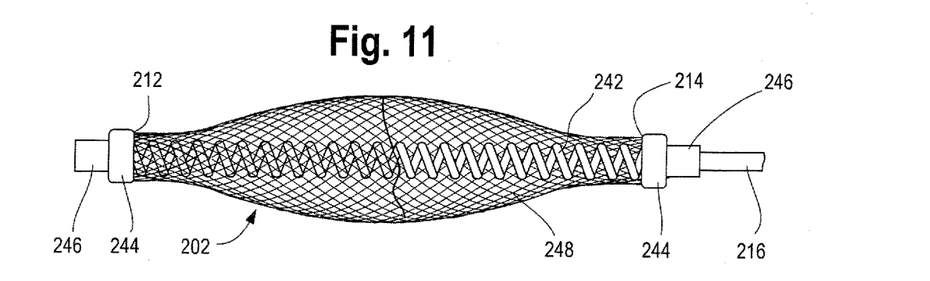
Figure 12:
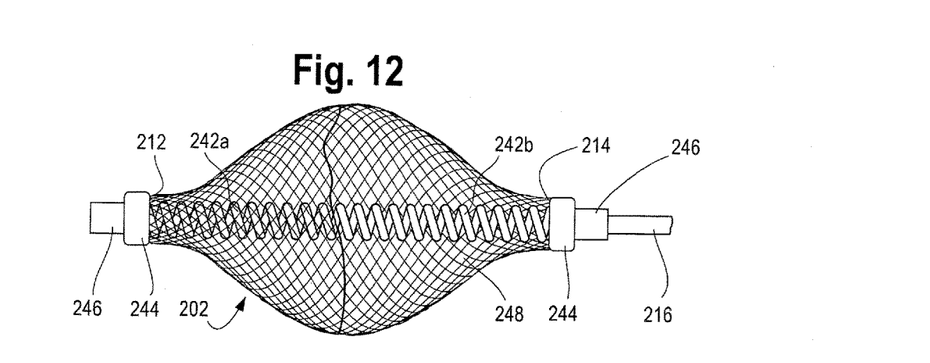
FIG. 12 shows the variable diameter dilating tip of FIG. 11 in an expanded diameter configuration.

FIG. 11 shows one example of a mechanically expandable variable diameter dilator tip 202 in a reduced-diameter configuration. FIG. 12 shows the variable diameter dilator tip 202 of FIG. 11 in an expanded-diameter configuration. For the sake of clarity, a flexible outer 240 surface has been omitted from FIGS. 11 and 12 so that the internal structure can be observed and described.

As shown in FIGS. 11 and 12, the delivery catheter 216 extends distally from the distal end 214 of the dilator tip 202. At least one biasing member 242 is disposed within the center of dilator tip 202 and can extend longitudinally from the proximal end 212 to the distal end 214 of the dilator tip 202. In one example, the biasing member 242 is a coil spring. One or more collars 244 may extend circumferentially around and crimp down the proximal and distal ends 212, 214 of the dilator tip 202 and a hub 246 may be secured to the collar 244.

Extending around the biasing member 242 between the proximal and distal ends 212, 214 of the tip 202 is an expandable and contractible structure 248. The structure 248 may be comprised of one or more fingers, wires, coils, fabrics, fibers, flexible arcuate members, cages, screens, disks, walls and the like, and may be constructed or formed from a single material or, alternatively, may be formed from a variety or combination of materials. In one example, at least a portion of structure 248 may be formed of any suitable material that may be expanded, such as by mechanical expansion. In other examples, at least a portion of the structure 248 may be formed from any suitable material that will result in self-expansion, such as shape memory material. As shown in FIGS. 11 and 12, the structure 248 is a mesh. A flexible outer surface or member 240 (shown in FIGS. 9 and 10 but removed from FIGS. 11, 11A and 12) may cover the mesh structure 248.

Dilating tip 202 can be mechanically expanded and contracted such that the outer diameter of the dilating tip 202 can increase and decrease. Such radial outward expansion of the tip 202 may be achieved in several ways. First, in one example, one or more resilient inner central elongate member(s) 242 extends between the proximal and distal hubs 246 as shown in FIGS. 11 and 12. The central elongate member 242 may include a coiled member or spring that extends substantially along the longitudinal axis. A proximal end of the elongate member 248 may be secured to the proximal hub 246 and a distal end of the elongate member may be secured to the distal hub 246.

The mesh structure 248 extends radially outwardly at a location that is generally centered between the respective hubs 246 to form a substantially conical, elliptical, ovoidal or egg-shape. The elongate member 248 may be biased in either an expanded condition or a contracted condition, thereby biasing the tip 202 in either a diameter reduced condition or a diameter expanded configuration, respectively. The elongate member 248 is also preferably longitudinally extensible such that it can be lengthened or stretched to facilitate a radially constricted reduced-diameter configuration as shown in FIG. 11. When the respective hubs 246 are extended away from each other in substantially opposing directions, the central elongate member 242 is extended. As a result, the dilator tip 202 becomes radially inwardly contracted. When the respective hubs 246 are moved towards each other, the central elongate member shortens. As a result, the dilator tip 202 becomes radially outwardly expanded as shown in FIG. 12.

Figure 11A:
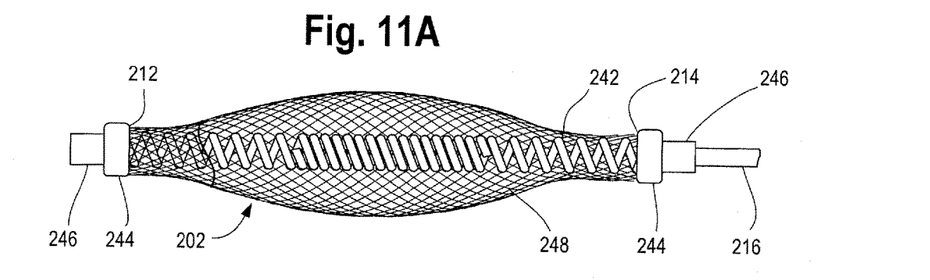

In another example, as shown generally in FIG. 11A, radial outward expansion of the dilator tip 202 may be achieved by providing two separate inner central elongate members, namely proximal elongate member 242a and distal elongate member 242b coupled to each of the respective hubs 246. The two central elongate members 242a and 242b may be in the form of springs or coils, or alternatively, two correspondingly shaped threaded members, one of which is configured to receive the other in a threadedly engaging manner. The two elongate members 242a and 242b preferably extend from each of the respective hubs 246 towards each other to a point where their respective terminating ends are adjacent and/or abut, and are capable of otherwise engaging each other. One of the elongate members 242b extending from the distal hub 246 may be rotated relative to the other elongate member 242a. Such rotation may be achieved by rotation of the delivery catheter 216 by the user, which, in turn, causes rotation of the distal elongate member 242b. Rotation of the distal elongate member 242b causes the two elongate members to engage each other (such as by one elongate member threadedly engaging the other elongate member) which, in turn, pulls the respective hubs 246 towards each other along the longitudinal axis. As the hubs 246 are pulled towards each other, the woven mesh 248 becomes extended radially outwardly at a location generally between the respective hubs 246 to form a radially outwardly expanded-diameter dilator tip 202 as illustrated in FIG. 12. Similarly, rotation of distal elongate member 242b (such as by rotation of the delivery catheter 216 in the opposite direction) causes the elongate members 242a and 242b to unthread or otherwise disengage, thus moving the respective hubs 246 longitudinally away from each other, such that dilator tip 202 may be returned to a radially-inwardly reduced-diameter configuration, as illustrated in FIGS. 11 and 11A. Expansion and contraction of the variable diameter tip 202 is further described in U.S. application Ser. No. 14/293,536, which is incorporated by reference herein.

Figures 13, 14:
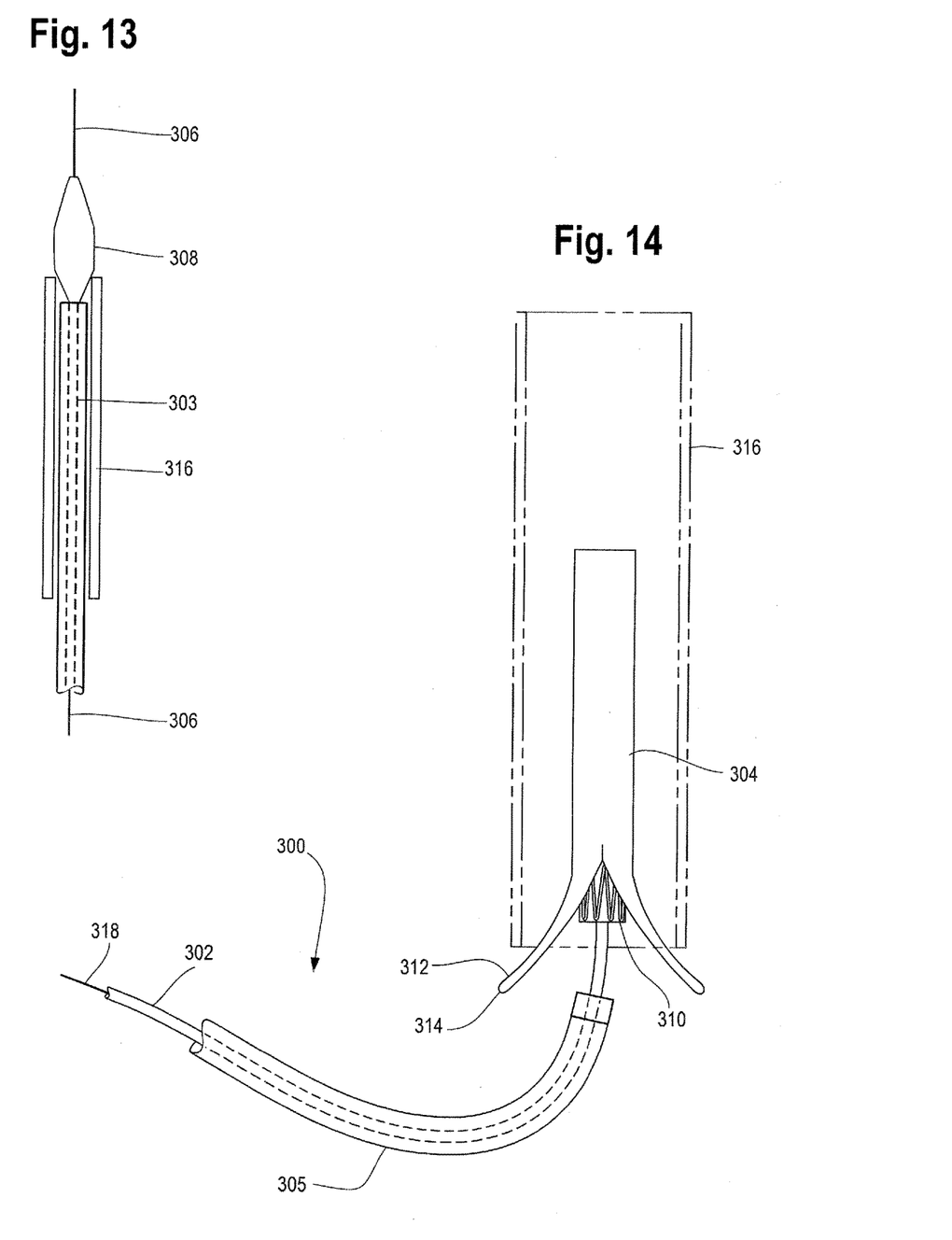
FIG. 13 illustrates a dilator and a delivery sheath that may be placed within a vessel during a procedure utilizing a cartridge technique.
FIG. 14 shows another example of an introducer with a peel-away sheath that may be tracked through the delivery sheath of FIG. 13 in a procedure utilizing a cartridge technique.

In yet another example, FIG. 13 illustrates an introducer 300 that can be tracked into place within a vessel and branched and/or fenestrated stent graft may also be pre-cannulated by the use of only a single wire. This may be achieved by utilizing an adaptation of a "cartridge" technique. This technique may be performed using a peel-away introducer sheath. FIG. 13 shows an example of an introducer 300 with a peel-away introducer sheath 304 for delivering and deploying a stent graft 310 using an adapted cartridge technique.

A guide wire 306 can first be inserted percutaneously into a patient's vasculature via a needle by known techniques. A delivery sheath 316, coaxial with a dilator of sufficient size 303, can be tracked over the guide wire 306 to the desired location in the vessel. The dilator 303 may have a nose cone 308 at its proximal end to provide an atraumatic tip for navigating the dilator 303 to a desired location within a vessel. The dilator 303 with the nose cone 308 at its proximal end can then be removed from the vasculature, leaving the sheath 316 in place. Sheath 316 can then serve as a conduit through which introducer 300 can be inserted.

A stent graft 310, loaded on the proximal end of a delivery catheter 302 and constrained under a peel-away sheath 304, can then be inserted in and through a hemostatic valve (not shown) near the distal end (not shown) of the delivery sheath 316 and pushed forward or proximally through the delivery sheath (such as by a pusher catheter 305) to the intended deployment location within a patient's vasculature. Once there, a user can push the stent graft proximally and out of the proximal end of the peel away sheath 304 using pusher 305, or alternatively, the user may remove the peel-away sheath 304 (distally) from the stent graft 310 by using the ends 312 of the peel-away sheath 304 as handles and pulling them distally so that the peel-away sheath 304 separates longitudinally and splits at the distal end 314. Next, a user can then distally pull (withdraw) the pull-away sheath 304 allowing the stent graft 310 to radially outwardly expand and deploy within the vessel.

Thus, when the stent graft 310 (loaded on the delivery catheter 302 within the peel-away sheath 304) is inserted through the delivery sheath 316 that has already been tracked into place within the vessel, a second guide wire and dilator tip may be eliminated. In other words, the delivery sheath 316 provides a conduit through which the delivery catheter 302 may be inserted, thus, the need for another wire and/or dilating tip may be unnecessary. Alternatively, the introducer 300 may comprise a stent graft 310 (such as a branched stent graft 34 or a fenestrated stent graft 78 as described above) that is pre-loaded with a wire 318 so that once the stent graft 310 has been tracked to the desired location within a vessel and removed from the peel away sheath 304, the wire 318 may be manipulated by the user to cannulate one or more branch vessels extending from the main vessel 1.

In one example, the introducer assembly 300 is used in the aortic arch. The stent graft may be a singular tube, a fenestrated stent graft or a branched or bifurcated stent graft. The wire 318 can be passed through a branch or fenestration of the stent graft 310 as generally described above. Once the stent graft 310 is deployed, the guide wire 318 will be in place to perform any necessary cannulation of a branch vessel extending from the main vessel. In this way, the introducer 300 can be tracked into place within delivery sheath 316 and the stent graft branch and/or fenestration may also be pre-cannulated by the use of only a single wire.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A nose cone dilator for a prosthesis delivery device, the nose cone dilator comprising:
   a proximal end having a proximal opening, a distal end, and a sidewall extending between the proximal and distal ends;
   a substantially straight internal lumen extending through the nose cone dilator between the proximal opening and the distal end;
   an opening formed in the sidewall;
   an angled internal channel extending from the opening formed in the sidewall to the proximal opening,
   wherein a length of the internal channel extending between the opening formed in the sidewall and the proximal opening is greater than an inner diameter of the channel measured adjacent to the opening formed in the sidewall; and wherein the angled internal channel extends to the substantially straight internal lumen and is in fluid communication with the substantially straight internal lumen.

2. The nose cone dilator of claim 1, wherein the internal channel has a curve imparted to at least a portion of it.

3. The nose cone dilator of claim 1, wherein the internal channel extends through the nose cone and wherein a proximal portion of the channel is parallel with the substantially straight lumen and wherein a distal portion of the channel is angled relative to the substantially straight lumen.

4. The nose cone dilator of claim 1, wherein the substantially straight lumen and the internal channel intersect each other.

5. The nose cone dilator of claim 4, wherein the substantially straight lumen and the internal channel intersect within the nose cone to generally form a "Y" shape.

6. The nose cone dilator of claim 1, wherein the internal channel extends through the nose cone the entire distance between the proximal opening of the nose cone and the opening formed in the sidewall.

7. A pre-loaded prosthesis delivery device comprising:
a delivery catheter having a proximal end,
a prosthesis releasably coupled to the proximal end of the delivery catheter, wherein the prosthesis has a proximal end, a distal end, and a lumen extending there between,
a nose cone dilator extending from the proximal end of the delivery catheter, wherein the nose cone comprises a proximal end having a proximal opening, a distal end, and a sidewall extending between the proximal and distal ends, a substantially straight internal lumen extending through the nose cone dilator between the proximal opening and the distal end, an opening formed in the sidewall, an angled internal channel extending from the opening formed in the sidewall to the proximal opening, wherein a length of the internal channel extending between the opening formed in the sidewall and the proximal opening is greater than an inner diameter of the channel measured adjacent to the opening formed in the sidewall and wherein the angled internal channel extends to the substantially straight internal lumen and is in fluid communication with the substantially straight internal lumen,
a secondary catheter having a delivery configuration and a released configuration, wherein, in the delivery configuration the secondary catheter extends through at least a portion of the prosthesis lumen, into the opening formed in the sidewall of the nose cone and extends at least partially into the internal channel formed in the nose cone, and in the released configuration the secondary catheter is retracted distally out of the internal channel formed in the nose cone dilator.

8. The prosthesis delivery device of claim 7 wherein the secondary catheter has a proximal end, a distal end and a lumen extending there between and wherein a guide wire extends at least partially through the lumen of the secondary catheter.

9. The prosthesis delivery device of claim 7 further comprising a fenestration formed in a sidewall of the prosthesis.

10. The prosthesis delivery device of claim 9 wherein an internal side branch extends distally from the fenestration formed in the sidewall of the prosthesis and into the lumen of the prosthesis.

11. The prosthesis delivery device of claim 10 wherein, in the delivery configuration, the secondary catheter extends proximally through at least a portion of the prosthesis lumen, through the internal side branch, exits through the fenestration formed in the sidewall of the prosthesis and extends further proximally and at least partially into the internal channel formed in the nose cone.

12. A method of delivering a prosthesis comprising;
tracking a prosthesis delivery device to a desired position within a main vessel lumen, the delivery device comprising
a delivery catheter having a tubular prosthesis releasably coupled thereto and
a nose cone extending from the proximal end of the delivery catheter, wherein the nose cone comprises a proximal end having a proximal opening, a distal end, and a sidewall extending between the proximal and distal ends, a substantially straight internal lumen extending through the nose cone dilator between the proximal opening and the distal end, an opening formed in the sidewall, an angled internal channel extending from the opening formed in the sidewall to the proximal opening and wherein a length of the internal channel extending between the opening formed in the sidewall and the proximal opening is greater than an inner diameter of the channel measured adjacent to the opening formed in the sidewall and wherein the angled internal channel is in fluid communication with the substantially straight internal lumen, and
a secondary catheter extending through at least a portion of the tubular prosthesis and extending at least partially into the internal channel formed in the nose cone,
distally retracting the secondary catheter to release it from the internal channel,
manipulating the secondary catheter to cannulate a branch vessel extending from the main vessel.

13. The method of claim 12 wherein the guide wire extends at least partially through a lumen of the secondary catheter and wherein the guide wire is distally retracted through the internal channel formed in the nose cone when the secondary catheter is distally retracted from the internal channel.

* * * * *